US008936447B2

(12) United States Patent
Abal

(10) Patent No.: US 8,936,447 B2
(45) Date of Patent: Jan. 20, 2015

(54) IV PUMP DUAL PISTON DISPOSABLE CASSETTE AND SYSTEM

(75) Inventor: Daniel Abal, San Diego, CA (US)

(73) Assignee: Carefusion 303, Inc., San Diego, CA (US)

( * ) Notice: Subject to any disclaimer, the term of this patent is extended or adjusted under 35 U.S.C. 154(b) by 653 days.

(21) Appl. No.: 12/869,612

(22) Filed: Aug. 26, 2010

(65) Prior Publication Data

US 2012/0053557 A1 Mar. 1, 2012

(51) Int. Cl.
| A61M 5/145 | (2006.01) |
| F04B 9/04 | (2006.01) |
| F04B 49/22 | (2006.01) |
| A61M 5/142 | (2006.01) |
| A61M 5/14 | (2006.01) |

(52) U.S. Cl.
CPC ........... *A61M 5/1422* (2013.01); *A61M 5/1413* (2013.01); *A61M 5/14216* (2013.01); *A61M 2205/128* (2013.01); *A61M 2205/12* (2013.01)
USPC ............................ 417/510; 417/534; 604/151

(58) Field of Classification Search
CPC . A61M 5/142; A61M 5/145; A61M 2205/12; A61M 2205/121; F04B 9/04; F04B 9/109
USPC .......... 417/510, 404, 487, 534; 604/131, 151; 222/276
See application file for complete search history.

(56) References Cited

U.S. PATENT DOCUMENTS

| 3,985,133 | A | * | 10/1976 | Jenkins et al. ................... 604/67 |
| 4,646,781 | A | * | 3/1987 | McIntyre et al. .......... 137/512.4 |
| 4,808,167 | A | * | 2/1989 | Mann et al. .................... 604/151 |
| 4,838,860 | A | | 6/1989 | Groshong et al. |
| 4,840,542 | A | | 6/1989 | Abbott |
| 4,898,579 | A | * | 2/1990 | Groshong et al. .............. 604/67 |
| 5,884,590 | A | | 3/1999 | Minculescu |
| 6,431,694 | B1 | | 8/2002 | Ross |
| 8,182,247 | B2 | * | 5/2012 | Gallwey et al. ............... 417/521 |
| 2004/0151594 | A1 | * | 8/2004 | Allington et al. ............... 417/12 |

FOREIGN PATENT DOCUMENTS

| EP | 1634612 A1 | 3/2006 |
| JP | 2008-038885 | 2/2008 |
| KR | 10-0917320 | 9/2009 |

* cited by examiner

*Primary Examiner* — Devon Kramer
*Assistant Examiner* — Nathan Zollinger
(74) *Attorney, Agent, or Firm* — McDermott Will & Emery LLP

(57) ABSTRACT

A cassette has an interface element having a first position and a second position. The interface element is configured to be driven from the first position to the second position and back to the first position by unidirectional rotary motion of a driving element. The cassette also has a first and a second pumping chamber each having a volume and each coupled to the interface element such that the volume of the first pumping chamber is increasing while the volume of the second pumping chamber is decreasing as the interface element moves from the first position to the second position and the volume of the first pumping chamber is decreasing while the volume of the second pumping chamber is increasing as the interface element moves from the second position to the first position.

24 Claims, 8 Drawing Sheets

IV PUMP DUAL PISTON DISPOSABLE CASSETTE AND SYSTEM

BACKGROUND

1. Field

The present disclosure generally relates to systems and methods of pumping fluid and, in particular, relates to the delivery of medical fluid by an infusion pump.

2. Background

Infusion pumps have become commonplace within the healthcare world as a way to precisely administer intravenous (IV) fluids. Use of a pump in place of an elevated fluid container with a simple roller clamp to control the flow of the IV fluid allows more accurate and consistent control of the rate of delivery of the fluid to the patient.

The assembly of tubing, valves, fittings, and needles that connect the fluid container to the patient may be referred to as an "IV set." IV sets are typically disposable to reduce the risk of infection and contamination. When used with an infusion pump, the IV set includes a segment intended to be manipulated by the pump to cause the fluid to flow at a controlled rate. A typical IV pump system is shown in FIG. 1 that depicts a patient 10 receiving a medical fluid from a fluid container 14 through an IV set 18. A pumping segment (not shown) of IV set 18 is located inside pumping module 20 of IV pump 12. The pumping module is controlled by pump controller 16.

For a peristaltic type of IV pump, the pumping segment may be as simple as a length of tubing that is fitted into the pumping compartment. FIG. 2 depicts an example IV set 18 having a bag spike 2 configured to connect to an IV bag (not shown) and pierce the seal of the bag, a length of tubing 4, a pumping segment 8, another length of tubing 4, and, in this example, a needleless connector 6. Pumping segment 8 includes locating fittings 5A and 5B at the ends of pumping segment 8, wherein the locating fittings 5A-5B match features on pumping module 20 of FIG. 1 to properly locate and retain the pumping segment 18 in the pumping module 20. IV set 18 also includes a clamp 9 that, when closed, blocks flow through tube 4.

Many IV pumps use pumping techniques, such as the peristaltic manipulation of a flexible tube, that deliver intermittent flow rather than continuous flow. While this may average out to be the desired rate of delivery, the instantaneous delivery rate varies from zero to as much as twice the nominal rate. This becomes even more apparent at very low delivery rates, as the pumping technique may delivery a periodic bolus of medical fluid rather than the desired continuous delivery at the nominal rate. For some patients, such as neonatal patients, this level of variation may be unacceptable. It is desirable to be able to provide a more continuous delivery at a more constant flow rate.

Another challenge common to existing IV pumps is that the manipulation of the pumping segment repeatedly compresses a flexible element of the pumping segment and relies on the flexible material to recover its original shape between compression strokes. The amount of recovery of the original shape affects the internal volume of the flexible element and therefore the amount of fluid pumped per compression stroke.

SUMMARY

A dual-piston disposable disclosed herein includes a cassette that provides precise control over the rate of delivery of medical fluid through the use of a pair of pumping chambers that utilize positive-displacement reciprocating pistons that are coupled with fluid control valves and driven by a unidirectionally rotating drive. The cassette is produced from a relatively small number of parts, simultaneously reducing cost while increasing the reliability of operation.

Certain exemplary embodiments of the present disclosure include a cassette that comprises an interface element having a first position and a second position, the interface element configured to be driven from the first position to the second position and back to the first position by unidirectional rotary motion of a driving element having an axis of rotation, and a first and a second pumping chamber each having a volume and each coupled to the interface element such that the volume of the first pumping chamber is increasing while the volume of the second pumping chamber is decreasing as the interface element moves from the first position to the second position and the volume of the first pumping chamber is decreasing while the volume of the second pumping chamber is increasing as the interface element moves from the second position to the first position.

In another embodiment, an IV pump system is disclosed that comprises a cassette and an IV pump. The cassette comprises an interface element having a first position and a second position, a first and a second pumping chamber each having a volume and each coupled to the interface element such that the volume of the first pumping chamber is increasing while the volume of the second pumping chamber is decreasing as the interface element moves from the first position to the second position and the volume of the first pumping chamber is decreasing while the volume of the second pumping chamber is increasing as the interface element moves from the second position to the first position. The IV pump comprises a housing comprising an attachment location configured to accept and retain the cassette and a driving element configured to engage the interface element of the cassette when the cassette is retained in the attachment location. The interface element is configured to be driven from the first position to the second position and back to the first position by unidirectional rotary motion of the driving element.

In another embodiment, a method of delivering medical fluid is disclosed that comprises the steps of connecting an IV set that comprises a cassette that comprises an intake port, a delivery port, an interface element having a first position and a second position, the interface element configured to be driven linearly from the first position to the second position and back to the first position by unidirectional rotary motion of a driving element having an axis of rotation, a first and a second pumping chamber each having a volume and each coupled to the interface element such that the volume of the first pumping chamber is increasing while the volume of the second pumping chamber is decreasing as the interface element moves from the first position to the second position and the volume of the first pumping chamber is decreasing while the volume of the second pumping chamber is increasing as the interface element moves from the second position to the first position to a patient, connecting the IV set to a source of medical fluid, attaching the cassette of the IV set to an IV pump, expanding the first pumping chamber to accept medical fluid from the fluid source while collapsing the second pumping chamber to deliver medical fluid to the patient, and collapsing the first pumping chamber to deliver medical fluid to the patient while expanding the second pumping chamber to accept medical fluid from the fluid source.

BRIEF DESCRIPTION OF THE DRAWINGS

The accompanying drawings, which are included to provide further understanding and are incorporated in and constitute a part of this specification, illustrate disclosed embodiments and together with the description serve to explain the principles of the disclosed embodiments. In the drawings.

DETAILED DESCRIPTION

IV pumps are frequently configured to accept a portion of the IV set, called the pumping segment, and to provide pumping action through manipulation of the pumping segment. This pumping segment may simply be a portion of the tubing of the IV set or a pumping chamber molded from a flexible plastic. One of the challenges of these types of pumping systems is that the internal dimensions are not directly controlled in the manufacturing process and are subject to variation. Another challenge common to existing IV pumps is that the manipulation of the pumping segment repeatedly compresses a flexible element of the pumping segment and relies on the flexible material to recover its original shape between compression strokes. The amount of recovery of the original shape affects the internal volume of the flexible element and therefore the amount of fluid pumped per compression stroke.

The present disclosure provides a disposable cassette that comprises reciprocating pistons using rigid elements to define the internal volume for the pumping chamber, thereby providing precise control of the amount of fluid pumped per stroke. The simple and reliable interface to the drive system of the IV pump increases the ease of use by the nurse or other person administering the medical fluid.

In the following detailed description, numerous specific details are set forth to provide a full understanding of the present disclosure. It will be apparent, however, to one ordinarily skilled in the art that embodiments of the present disclosure may be practiced without some of the specific details. In other instances, well-known structures and techniques have not been shown in detail so as not to obscure the disclosure.

Figure 2:
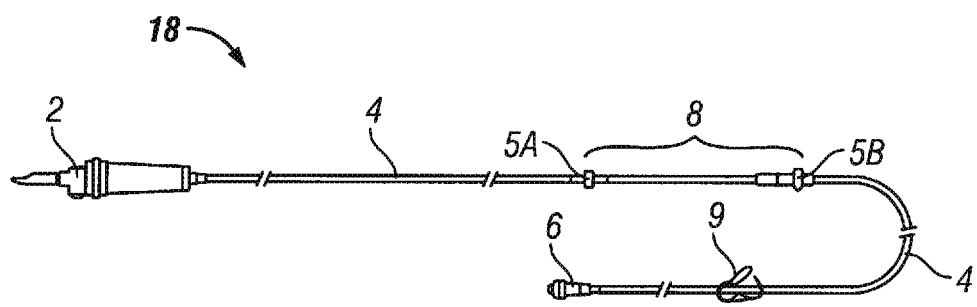
FIG. 2 is an example IV set for a peristaltic-type IV pump.
Figure 3:
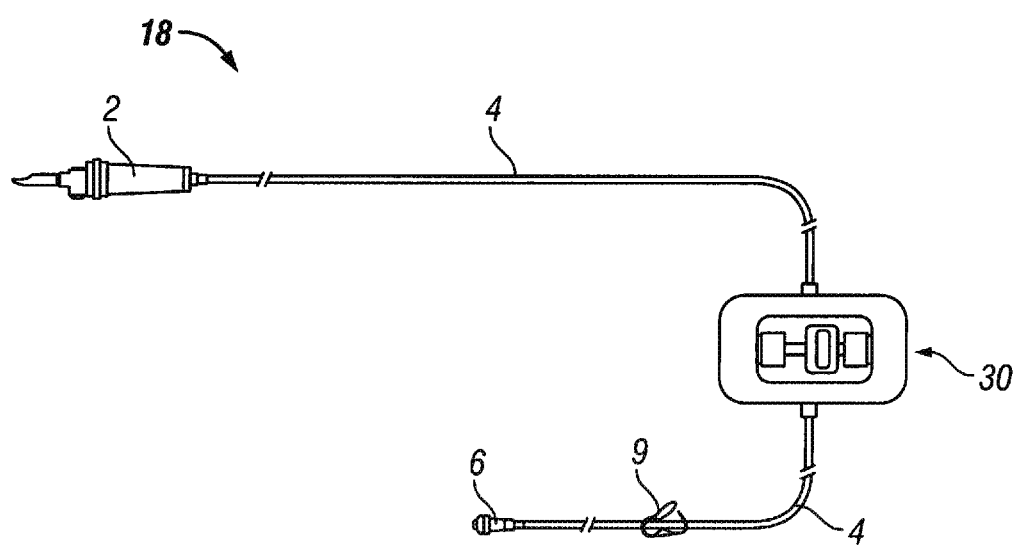
FIG. 3 depicts an embodiment of an IV set comprising a cassette according to certain aspects of the present disclosure.

FIG. 3 depicts an embodiment of an IV set 18 comprising a cassette 30 according to certain aspects of the present disclosure. IV set 18 comprises the same elements as shown in FIG. 2, including a bag spike 2, a needleless connector 6, and clamp 9. In other embodiments, other types of connectors may be provided at either end to connect to different systems and devices. In some embodiments, the IV set 18 comprises additional components such as a "Y site" needleless connector (not shown).

Figure 4A:
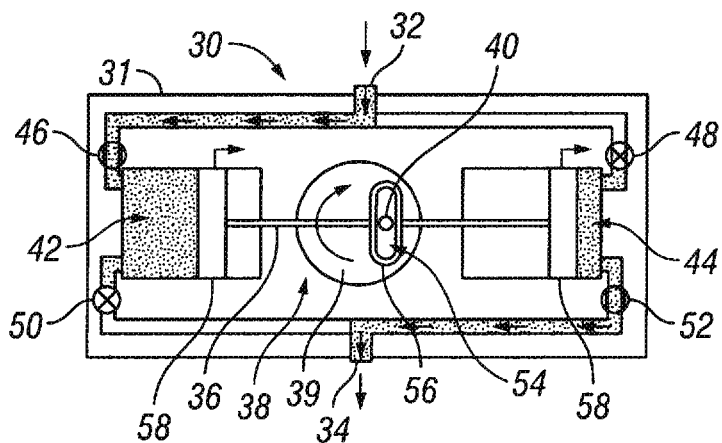
FIGS. 4A-4B are schematic representations of a cassette having dual reciprocating pistons according to certain aspects of the present disclosure.
Figure 4B:
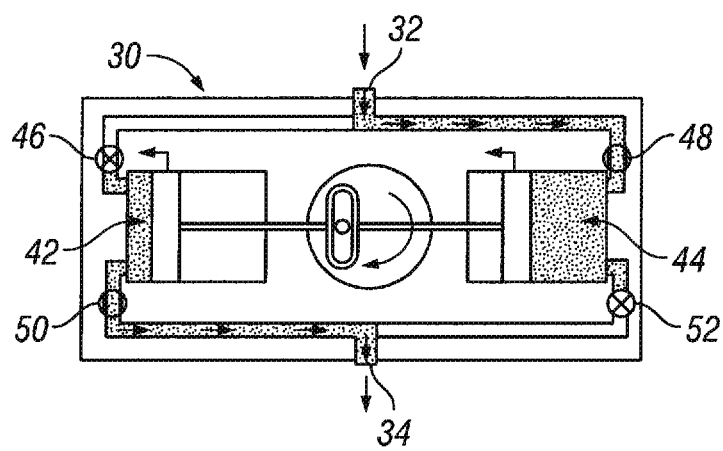

FIGS. 4A-4B are schematic representations of a cassette 30 having dual reciprocating pistons 58 according to certain aspects of the present disclosure. The cassette 30 has an inlet port 32 and a delivery port 34 that are, in this example, located at the top and bottom, respectively, (as seen in FIGS. 4A-4B) of the body 31. There are two pumping chambers 42 and 44 that are defined by bores in the body 31 and pistons 58. Inlet valves 46 and 48 are fluidically coupled between inlet port 32 and pumping chambers 42 and 44, respectively. Outlet valves 50 and 52 are fluidically coupled between pumping chambers 42 and 44, respectively, and delivery port 34. When actuated, the valves 46, 48, 50, and 52 stop the flow of fluid through the respective valve. The two pistons 58 are, in this example, rigidly coupled to an interface element 36 that is configured, in this example, to connect to a driving element 38 that comprises a disk 39 and a drive pin 40. The driving element 38 is shown in FIG. 4A in plan view and in a perspective view in FIG. 4C. Interface element 36 comprises a "Scotch yoke" 56 that comprises a slot 54, wherein pin 40 is a sliding fit in slot 54 such that pin 40 slides along the length of slot 54. The contact surface of the slot 54 is a low-friction material such as a plastic, nylon or acetal homopolymer for example, and the drive pin 40 comprises a hard, smooth surface, polished stainless steel for example, to reduce friction and ensure that the majority of the wear is in the yoke 56.

Figure 4C:
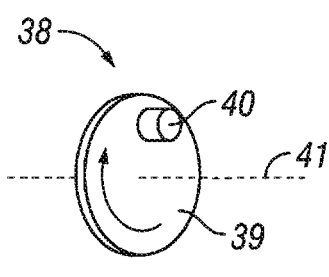
FIG. 4C is a perspective view of the drive element of an IV pump configured to use the cassette of FIGS. 4A-4B according to certain aspects of the present disclosure.

FIG. 4C is a perspective view of the drive element of an IV pump configured to use the cassette of FIGS. 4A-4B. In this embodiment, drive element 38 comprises a disk 39 that rotates about an axis of rotation 41. A drive pin 40 is attached to disk 39 at an offset from axis 41. The drive pin 40 is generally cylindrical, in this example, with the axis of symmetry of the cylindrical shape parallel to the axis of rotation 41.

At the moment of time that is depicted in FIG. 4A, inlet valve 46 and outlet valve 52 are open, indicated by the open channel across the valve symbol, while inlet valve 48 and outlet valve 50 are closed, indicted by the "x" across the valve symbol.

In operation, disk 39 will rotate, in this view, clockwise in the plane of the paper. Pin 40 follows a circular path around the center of rotation of disk 39 and pin 40 will move vertically, in this view, in slot 54 while simultaneously causing interface element 36 to move horizontally, in this view. As pistons 58 are rigidly coupled to interface element 36, the pistons 58 will also move horizontally. As pistons 58 move to the right, in this view, pumping chamber 42 expands and draws fluid from inlet port 32 through inlet valve 46 as indicated by the series of arrows from the inlet port 32 to pumping chamber 42. At the same time, pumping chamber 44 is contracting and forcing fluid to flow through outlet valve 52 to the delivery port 34 as indicated by the series of arrows from the pumping chamber 44 to delivery port 34.

If a reference frame for the angular position of the drive pin 40 is defined to be zero degrees when the drive pin 40 is located at the top of drive element 38, as seen in this view, then the peak flow will occur when the drive pin 40 is at the zero and 180 degree positions and will be momentarily zero when the drive pin 40 is at the 90 and 270 degree positions. When the drive pin 40 reaches the rightmost distance, at a 90 degree position in this view, the horizontal motion of the interface element 36 and the pistons will reverse. As the drive pin passes the 90 degree position, inlet valve 46 and outlet valve 52 close and inlet valve 48 and outlet valve 50 close and the system is in the configuration depicted in FIG. 4B.

As disk 39 continues to rotate clockwise, drive pin 40 will begin to move to the left, in this view, causing interface element 36 and pistons 58 to move to the left as well. Pumping chamber 42 will now be contracting and forcing fluid out through outlet valve 50 to delivery port 34. Pumping chamber 44 is expanding, drawing fluid from inlet port 32 through inlet valve 48.

In this embodiment, drive element 38 rotates at a constant angular velocity and therefore the linear motion of interface element 36 will be a sinusoid. The rate of change of volume of pumping chamber 42 and 44 is a direct function of the displacement of interface element 36 and, thus, the flow rate of fluid out of delivery port 34 will also be sinusoidal. In certain embodiments, the angular velocity of drive element 38 changes over the period of a rotation in order to produce a more constant flow of fluid out of delivery port 34. In certain embodiments, the angular velocity of drive element 38 has one value over most of the rotation and a second higher value when the drive pin 40 is near the 90 and 270 degree positions. In certain embodiments, the angular velocity of drive element 38 varies continuously over a rotation. In certain embodiments, the angular velocity of drive element 38 is approximately sinusoidal with the maximum angular velocity occurring at 90 and 270 degree positions.

Figure 4D:
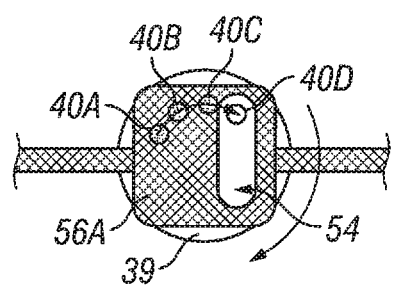
FIG. 4D is a plan view of a self-aligning yoke and drive pin according to certain aspects of the present disclosure.

FIG. 4D is a plan view of a self-aligning yoke 56A and drive pin 40 according to certain aspects of the present disclosure. In this embodiment, yoke 56A is large enough that pin 40 is covered continuously as disk 39 rotates except for slot 54. In this example, pin 40 is in position 40A and yoke 56A is in the position shown in FIG. 4D when cassette 30 is installed in pumping module 20. As can be seen, pin 40, in position 40A, is covered by the yoke 56A. In certain embodiments, pin 40 can slide into disk 39 to a depth where pin 40 is flush with the surface of disk 39. In some embodiments, drive element 38 comprises a biasing element (not shown), such as a spring, that urges pin 40 to move from the flush position to an extended position towards yoke 56A. In this example, the surface of cassette 30 that is shown in FIG. 5C is in contact with the surface of the recess 21 of FIG. 7. In the initial position where pin 40 is in location 40A, pin 40 is forced to the flush position with the surface of disk 39 by the surface of yoke 56A.

When IV pump 12 starts, disk 39 begins to rotate clockwise, in this example. As disk 39 rotates, pin 40 will sequentially be in positions 40B and 40C and then 40D. In positions 40B and 40C, pin 40 remains in the flush position and slides along the surface of yoke 56A. Yoke 56A remains stationary as the friction between pin 40 and the surface of yoke 56A is insufficient to move the interface element 36 and the coupled pistons 58. When pin 40 reaches position 40D, however, pin 40 is free to move to the extended position, wherein pin 40 protrudes into slot 54 and couples the drive element 38 with the interface element 36. From this point forward, the continued unidirectional rotation of drive element 38 will cause interface element 36 to oscillate linearly.

Figure 5A:
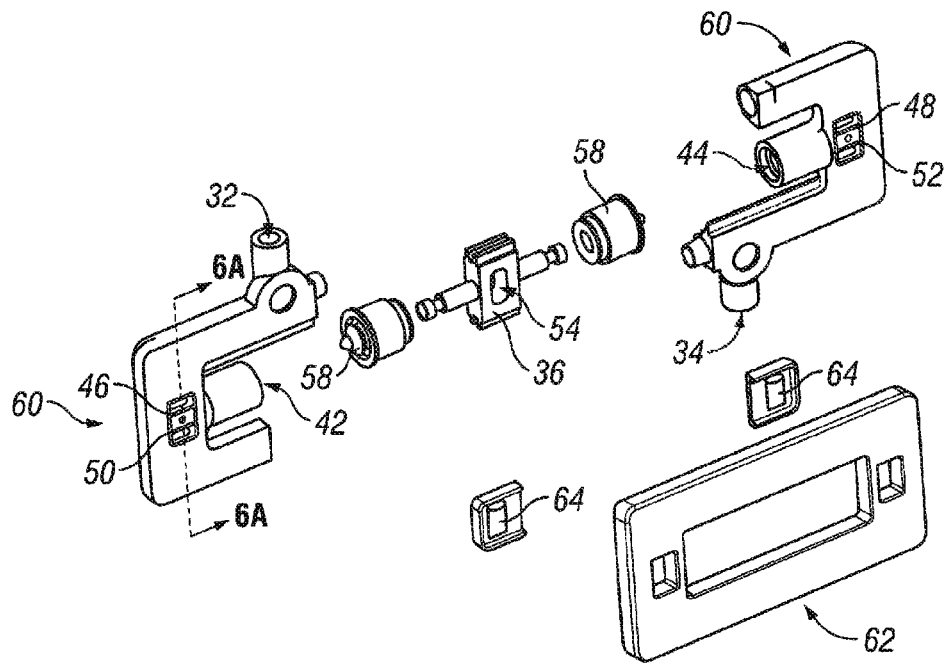
FIG. 5A is an exploded view of one embodiment of a cassette according to certain aspects of the present disclosure.

FIG. 5A is an exploded view of one embodiment of a cassette 30 according to certain aspects of the present disclosure. Two body elements 60 when connected together form inlet port 32, delivery port 34, the cavities that form pumping chambers 42 and 44, a portion of inlet valves 46 and 48 and outlet valves 50 and 52, and the interconnecting fluid channels that couple the valves to the respective ports and pumping chambers. An interface element 36 having a slot 54 is molded as a single piece. Pistons 58, in this example, comprise dust boots that fit over the outer walls of pumping chambers 42 and 44. Flexible elements 64 form a portion of the inlet 46, 48 and outlet valves 50, 52, as discussed in detail in FIGS. 6A-6C. Body elements 60 are mated to each other, capturing interface element 36 and pistons 58, and a cover 62 captures the flexible elements 64 against the body elements 60 to form the valves 46, 48, 50, and 52 as well as hold body elements 60 together. It can be seen that this exemplary cassette 30 is formed from only five different parts which are easily assembled without the need for adjustment or precision placement of any component, improving the reliability of the finished cassette 30. These parts may be formed from a variety of materials, including plastics such as polycarbonate, acetal homopolymer, polyester, and nylon. In certain embodiments, materials such as metal or ceramic may be desirable for some parts to provide, for example, increased wear resistance, chemical resistance, or durability. In some embodiments, a material such as polytetrafluoroethylene may be desirable for some parts to provide lubricity and sealing capability. As the individual parts are self-aligning to the mating parts, fixturing is not required and the risk of incorrect assembly is reduced. In certain embodiments, components are attached to each other with a process such as ultrasonic welding, laser welding, thermal bonding or staking, or mechanical staking or crimping. In certain embodiments, components are attached with fasteners such as screws or rivets. In certain embodiments, adhesive or other bonding materials are used to bond some components together. In certain embodiments, a sealant is used to seal mating surfaces to form a liquid-tight joint.

Figure 5B:
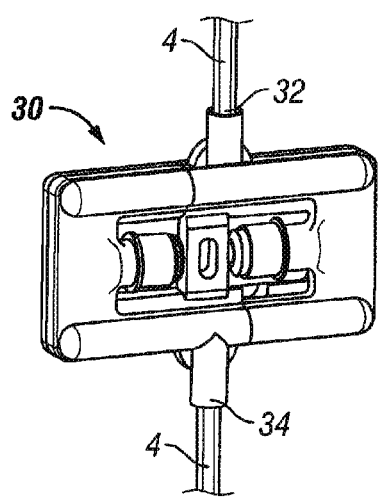
FIGS. 5B-5C depict front and rear views of the assembled cassette of FIG. 45A according to certain aspects of the present disclosure.
Figure 5C:
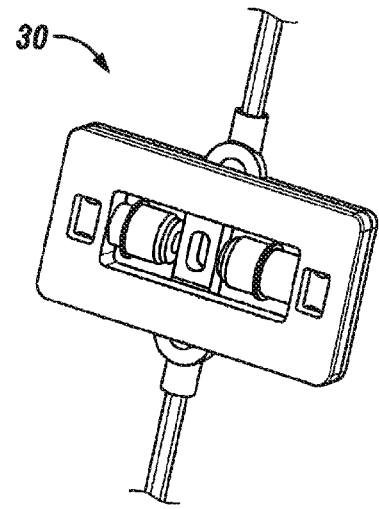

FIGS. 5B-5C depict front and rear views of the assembled cassette of FIG. 5A according to certain aspects of the present disclosure. In FIGS. 5B and 5C, tubing 4 has been attached to the inlet port 32 and delivery port 34 to form an IV set as shown in FIG. 3. FIG. 5C depicts the face of cassette 30 that faces the pumping module 20, as is further discussed in FIG. 7.

Figure 6A:
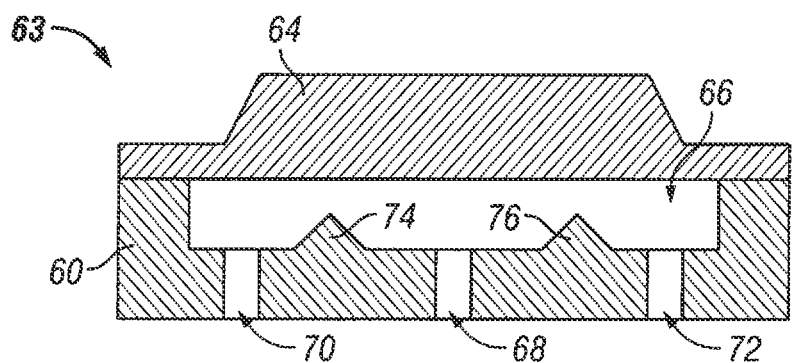
FIG. 6A illustrates a cross-section of a portion of a fluid control valve assembly according to certain aspects of the present disclosure.

FIG. 6A illustrates a cross-section according to line 6A-6A in FIG. 5A (including flexible element 64 and cover 62 as assembled in FIG. 5B-5C) of a fluid control valve assembly 63 according to certain aspects of the present disclosure. The fluid control valve assembly 63 is resistant to collapse under a reduced internal pressure, unlike valves wherein a flexible tube is compressed to shut off flow as the flexible tube is prone to collapse if the internal pressure is lower than the external ambient pressure. The combination of this type of fluid control valve 63 with the rigid body elements 60 provides the capability for the cassette 30 to create a reduced pressure at the inlet 4 as either pumping volume 42 or 44 expand. Body element 60 incorporates a chamber 66 with three ports 68, 70, and 72. Port 68 is fluidically coupled to, in this example, pumping chamber 42. There is a second fluid control valve assembly (not shown) associated with pumping chamber 44. In this example, port 70 is fluidically coupled to inlet 32 and port 72 is fluidically coupled to delivery port 34. Ridges 74 and 76 are formed across cavity 66 in body 60. Flexible element 64 covers cavity 66 and is sealed to body 60 around the periphery of cavity 66, forming a sealed chamber.

Figure 6B:
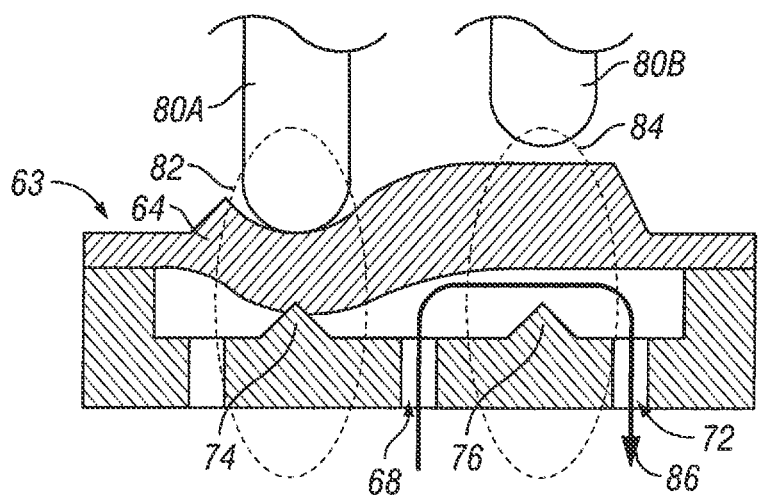
FIGS. 6B-6C illustrate the operation of the fluid control valve assembly of FIG. 6A according to certain aspects of the present disclosure.
Figure 6C:
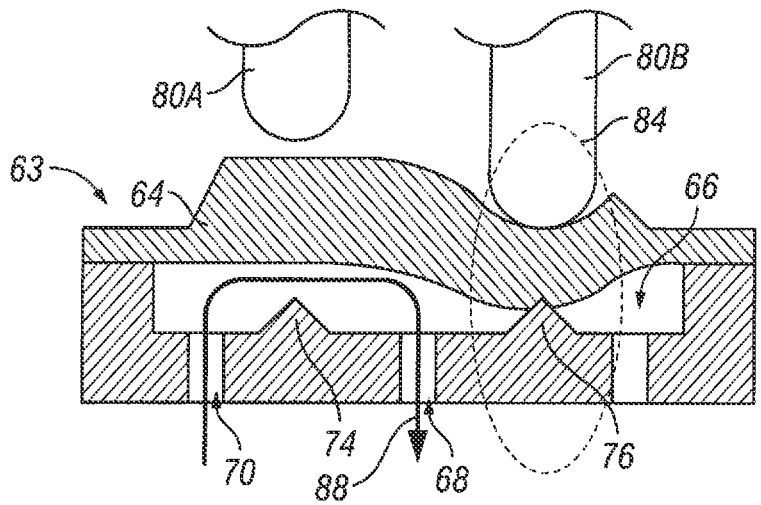

FIGS. 6B-6C illustrate the operation of the fluid control valve assembly 63 of FIG. 6A according to certain aspects of the present disclosure. Pumping module 20 comprises valve actuators 80A and 80B external to cassette 30 that are configured to move from a retracted position, such as that of actuator 80B in FIG. 6B, to an extended position, such as that of actuator 80A in FIG. 6B. In the extended position, flexible element 64 is forced against the ridge under the extended actuator, such as is shown in FIG. 6B wherein actuator 80A is extended and pressing flexible element 64 against ridge 74, stopping fluid flow past ridge 74. As such, the region of body element 60 and flexible element 64 indicated by the broken-line oval 82 forms inlet valve 46 of FIG. 4A while the broken-line oval 84 indicates the portions of body element 60 and flexible element 64 that form outlet valve 50.

FIG. 6B depicts the configuration of the fluid control valve assembly 63 when pumping chamber 42 is contracting, forcing fluid into chamber 66 through port 68. As actuator 80A has sealed flexible element 64 against ridge 74, the fluid will flow past ridge 76 and out through port 72 to the delivery port 34 as indicated by arrow 86.

FIG. 6C depicts the configuration of the fluid control valve assembly 63 when pumping chamber 42 (not shown) is expanding, drawing fluid out of chamber 66 through port 68. As actuator 80B has sealed flexible element 64 against ridge 76, fluid will be drawn in from the inlet port 32 through port 70 and past ridge 74 as indicated by arrow 88.

Figure 7:
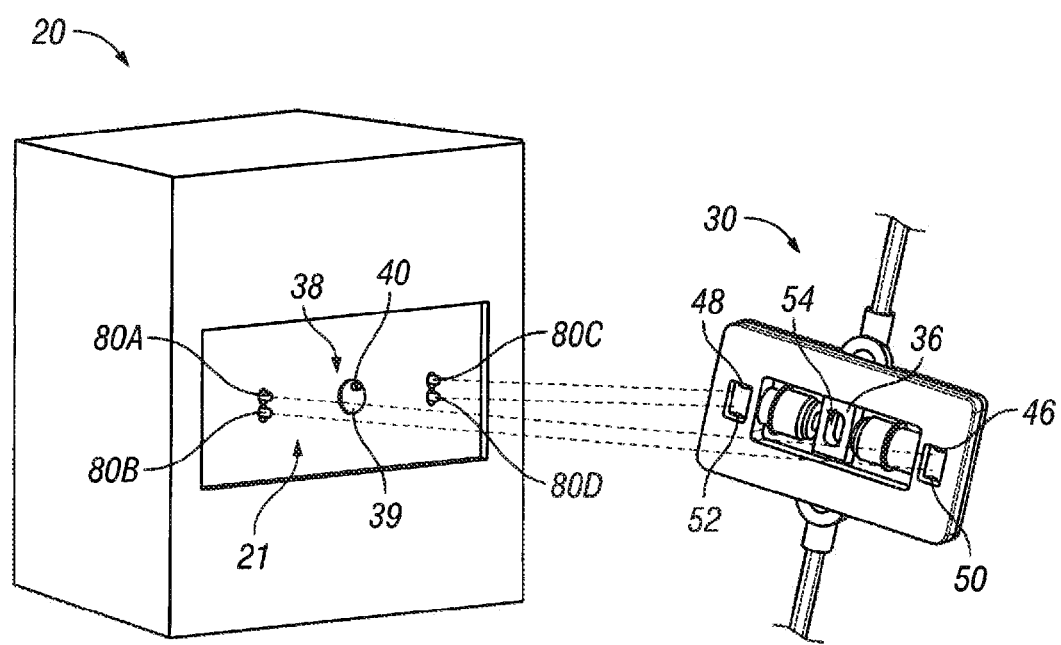
FIG. 7 illustrates certain elements of a pumping module configured to use the cassette of FIGS. 5B-5C according to certain aspects of the present disclosure.

FIG. 7 illustrates the features of a pumping module 20 configured to use the cassette 30 of FIGS. 4B-4C according to certain aspects of the present disclosure. Pumping module 20 comprises a recess 21 configured to accept cassette 30 wherein drive element 38 is configured to engage interface element 36. In this example, drive element 38 comprises a rotating disk 39 and pin 40, wherein the pin 40 engages slot 54. Pumping module 20 further comprises four valve actuators 80A, 80B, 80C, and 80D. Actuators 80A and 80B actuate inlet valve 46 and outlet valve 50, respectively, as discussed in FIGS. 6A-6C. Similarly, actuators 80C and 80D actuate inlet valve 48 and outlet valve 52, respectively. In certain embodiments, the motion of the actuators 80A-80D are synchronized with the unidirectional rotation of drive element 38. In certain embodiments, drive element 38 comprises a cam (not shown) that drives the actuators such that a single drive motor (not shown) of pumping module 20 provides both pumping motion of the pistons 58 and operation of the valves 46, 48, 50, and 52, reducing the complexity of the system and increasing the reliability of operation.

Figure 8:
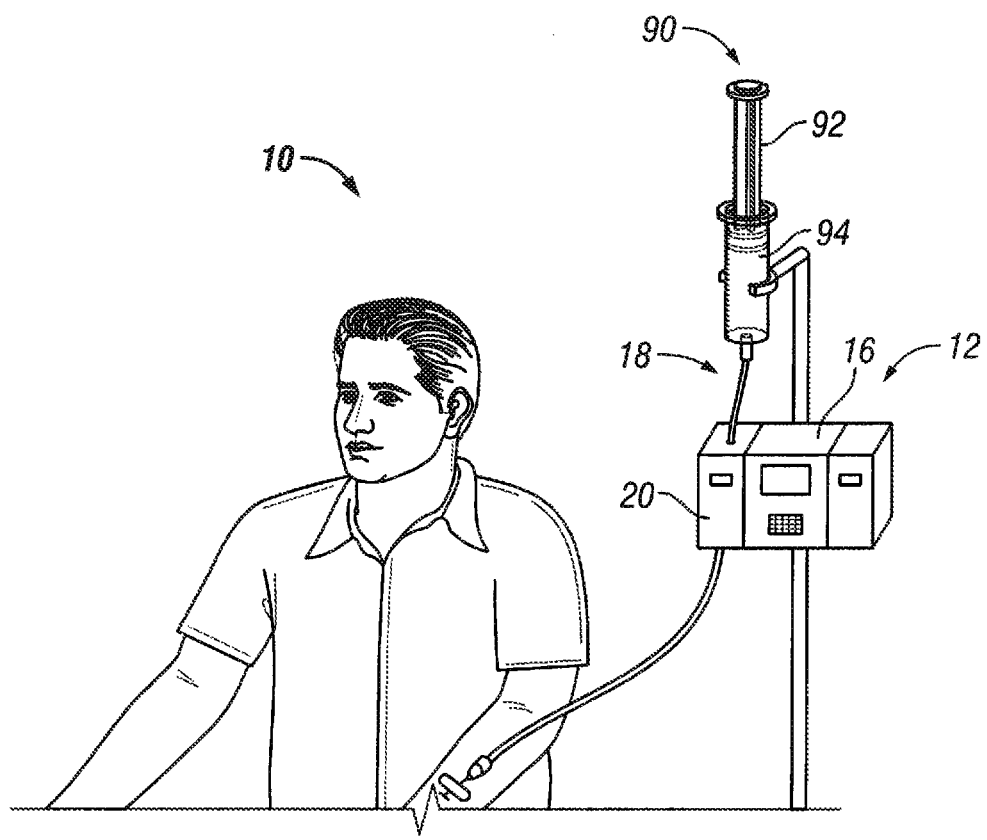
FIG. 8 depicts a patient receiving an infusion of medical fluid from a syringe through an IV pump according to certain aspects of the present disclosure.

FIG. 8 depicts a patient receiving an infusion of medical fluid from a syringe 90 through an IV pump 12 according to certain aspects of the present disclosure. Syringes are sometimes used to provide a small quantity of medical fluid or medication, or to provide a medical fluid that is not available in an IV bag 14. A syringe 90 may be sealed or vented. A vented syringe functions similar to a vented IV bag 14, as air enters the container to replace the fluid drawn into the IV pump 12. A sealed syringe, however, requires a partial vacuum, e.g. a reduced pressure within the system compared to the ambient pressure, to withdraw fluid from the syringe as the plunger 92 must be drawn into the barrel 94 by the reduced pressure. A reduced pressure of approximately 5 pounds per square inch is necessary to enable the use of a sealed syringe as a fluid source. Other types of pumping modules, such as the peristaltic tube pumping section 8 of FIG. 2, may collapse when the internal pressure drops below the external ambient pressure, whereas the cassette 30 (not shown in FIG. 8) is capable of creating a pressure that is at least 5 PSI below ambient pressure and therefore is capable of drawing fluid from a sealed syringe 90.

Figure 9:
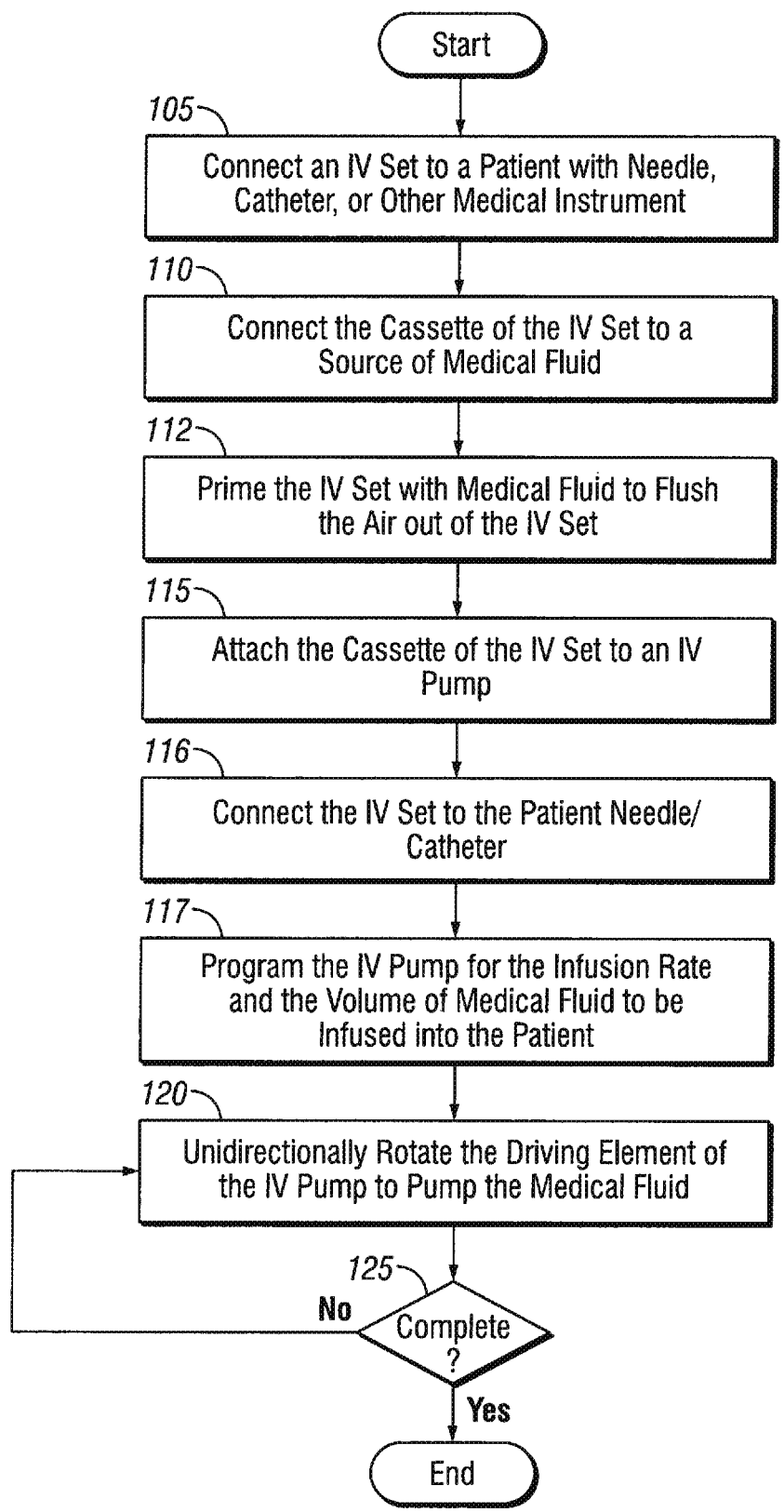
FIG. 9 is a flow chart of a method for providing a medical fluid to a patient according to certain aspects of the present disclosure.

FIG. 9 is a flow chart that describes a method of providing a medical fluid to a patient 10 according to certain aspects of the present disclosure. While this method is presented in the context of a nurse administering a medical fluid in a hospital setting, it is equally applicable to other caregivers in other settings, including self-administered medical fluids.

Figure 1:
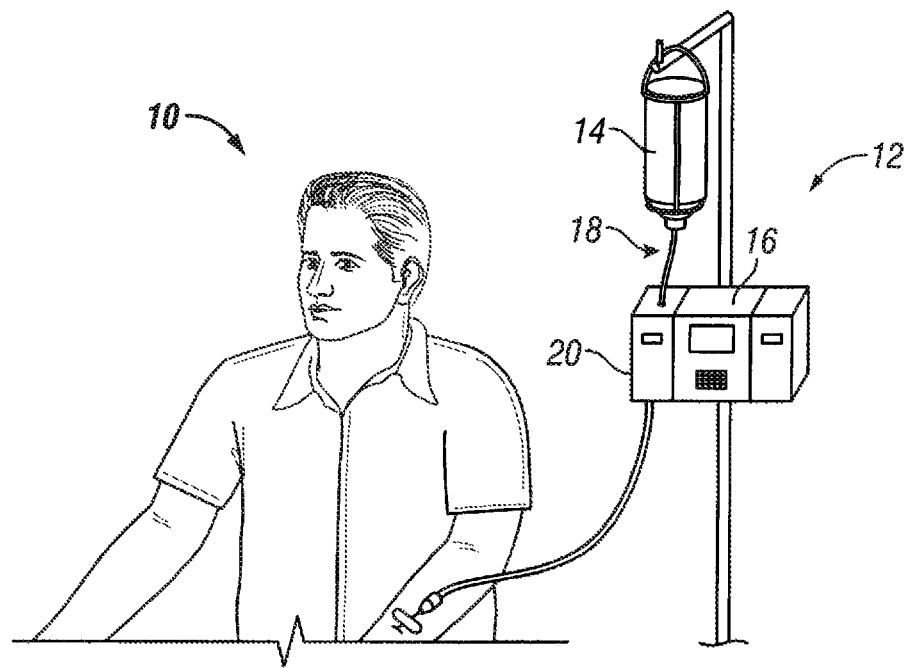
FIG. 1 depicts a patient receiving an infusion of medical fluid through an IV pump.

In step 105, the nurse connects an IV set 18 that comprises a cassette 30 as described herein to a patient 10. This may be accomplished using a variety of medical instruments, such as an infusion needle, that may be coupled to the IV set 18 via a variety of apparatus, such as needleless connectors, that are well known to those of skill in the art. The nurse then, in step 110, connects the IV set 18 to a source of medical fluid. In certain configurations, the source of medical fluid is a fluid container 14 as shown in FIG. 1, wherein the connection is accomplished with a bag spike 2 as shown in the IV set 18 of FIG. 3. The nurse then in step 112 primes the IV set with medical fluid to flush the air out of the IV set. In certain embodiments, the source of medical fluid is a syringe. In certain embodiments, the syringe is sealed and the cassette creates a negative pressure, relative to ambient pressure, to draw the plunger into the syringe as the fluid is withdrawn from the syringe. In certain embodiments, this negative pressure is greater than 5 PSI. In step 115, the nurse attaches the cassette 30 to the pumping module 20 of IV pump 12. After the IV set is ready, the nurse in step 116 connects the IV set that is connected to the source of medical fluid to the portion of the IV set or needle that is connected to the patient. In step 117, the nurse configures the IV pump to deliver the medical fluid at the appropriate rate and, in step 120, starts the IV pump 12 and the driving element 38 unidirectionally rotates and drives the interface element 36 to oscillate, causing the first pumping chamber 42 of the cassette 30 to accept medical fluid from the fluid source 14 while collapsing the second pumping chamber 44 to deliver medical fluid to the patient 10. When interface element 36 reaches the end of its motion in this first direction, interface element 36 reverses direction as driven by the unidirectional rotary motion of driving element 38 and the first pumping chamber 42 contracts and pumps medical fluid to the patient 10 while the second pumping chamber 44 expands to accept medical fluid from the fluid source 14. If at any time, the delivery of medical fluid is complete, decision step 125 branches along the "yes" path to the end. If the delivery is not complete, decision step 125 branches along the "no" path to step 120. Step 120 repeats until the delivery of medical fluid is complete.

It can be seen that the disclosed embodiments of the IV pump dual-piston disposable provide precise delivery of medical fluids to patients using a low-cost disposable. Driving the reciprocating linear motion of the pistons from a unidirectionally rotating drive reduces the number of drive components and sensing elements required to pump the fluid, improving the reliability of the system. Driving the valve actuators from a cam connected to the same motor that drives the pumping action further simplifies the IV pump, reducing cost while improving the operational reliability. The straightforward and elegant design of the cassette, formed from only five unique parts that are self-aligning in assembly, provides a low-cost and highly reliable disposable IV set.

While the present disclosure describes a dual-piston pumping element in the context of its use as part of disposable IV set used with an IV pump for delivery of medical fluid in a healthcare setting, this same system and method may be used in a variety of other applications, particularly where it is desirable to have near-continuous delivery of fluid or where a low-cost and reliable means of pumping fluid is beneficial. Furthermore, while this system is presented as a disposable pumping element, the same techniques and methods may be utilized in a non-disposable system to provide the same advantages in pumping fluid. Nothing disclosed herein is intended to limit the field of application of this system or method unless such disclosure is explicitly recited in the claims.

The previous description is provided to enable any person skilled in the art to practice the various aspects described herein. While the foregoing has described what are considered to be the best mode and/or other examples, it is understood that various modifications to these aspects will be readily apparent to those skilled in the art, and the generic principles defined herein may be applied to other aspects. Thus, the claims are not intended to be limited to the aspects shown herein, but is to be accorded the full scope consistent with the language claims, wherein reference to an element in the singular is not intended to mean "one and only one" unless specifically so stated, but rather "one or more." Unless specifically stated otherwise, the terms "a set" and "some" refer to one or more. Pronouns in the masculine (e.g., his) include the feminine and neuter gender (e.g., her and its) and vice versa. Headings and subheadings, if any, are used for convenience only and do not limit the invention.

It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

Terms such as "top," "bottom," "front," "rear" and the like as used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

A phrase such as an "aspect" does not imply that such aspect is essential to the subject technology or that such aspect applies to all configurations of the subject technology. A disclosure relating to an aspect may apply to all configurations, or one or more configurations. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. A phrase such an embodiment may refer to one or more embodiments and vice versa.

The word "exemplary" is used herein to mean "serving as an example or illustration." Any aspect or design described herein as "exemplary" is not necessarily to be construed as preferred or advantageous over other aspects or designs.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. §112, sixth paragraph, unless the element is expressly recited using the phrase "means for" or, in the case of a method claim, the element is recited using the phrase "step for." Furthermore, to the extent that the term "include," "have," or the like is used in the description or the claims, such term is intended to be inclusive in a manner similar to the term "comprise" as "comprise" is interpreted when employed as a transitional word in a claim.

What is claimed is:

1. A cassette comprising:
    an interface element having a first position and a second position and a slot that is oriented perpendicular to a direction of linear motion of the interface element between the first and second positions;
    the interface element configured to be driven from the first position to the second position and back to the first position by unidirectional rotary motion of a driving element comprising an axis of rotation and a drive pin that is parallel to and offset from the axis of rotation and disposed within the slot such that the drive pin slides along a portion of the slot as the driving element rotates;
    a first and a second pumping chamber each having a volume and each coupled to the interface element such that the volume of the first pumping chamber is increasing while the volume of the second pumping chamber is decreasing as the interface element moves from the first position to the second position and the volume of the first pumping chamber is decreasing while the volume of the second pumping chamber is increasing as the interface element moves from the second position to the first position;
    an intake port and a delivery port;
    a first and a second inlet valve coupled between the intake port and the respective pumping chambers; and
    a first and a second outlet valve coupled between the respective pumping chambers and the delivery port,
    wherein the inlet valves and the outlet valves are configured to be actuated via one or more elements disposed on an actuator-facing surface of the cassette and to provide a continuous flow between the intake port and the delivery port.

2. The cassette of claim 1, wherein the drive pin follows a circular path about the axis of rotation as the driving element rotates.

3. The cassette of claim 2, wherein:
    the slot has a length that is oriented perpendicular to the direction of linear motion of the interface element between the first and second positions; and
    the drive pin slides along a portion of the length of the slot as the driving element rotates.

4. The cassette of claim 3, wherein the interface element comprises a Scotch yoke.

5. The cassette of claim 1, wherein the cassette has a total internal volume between the intake port and the delivery port, and wherein the cassette is configured to create, when the driving element moves from either the first position to the second position or from the second position to the first position, a negative pressure at the intake port of at least 5 pounds per square inch below ambient pressure without a change in the total internal volume of the cassette.

6. The cassette of claim 1, wherein the pumping chambers each comprise a cylinder having a bore that is closed at one end and a piston configured to slide along the bore, wherein the volume of each pumping chamber is defined by the space within the cylinder bounded by the closed end and each piston.

7. The cassette of claim 6, wherein the pumping chambers each further comprise a sliding seal between the respective piston and cylinder.

8. The cassette of claim 6, wherein the bores of the first and second pumping chambers are aligned and the pistons are rigidly connected to each other.

9. The cassette of claim 1, further comprising:
a length of intake tubing having a first end and a second end, wherein the first end is coupled to the intake port;
a length of delivery tubing having a first end and a second end, wherein the first end is coupled to the delivery port;
a first connection device coupled to the first end of the intake tubing; and
a second connection device coupled to the first end of the delivery tubing;
wherein the cassette, the intake and delivery tubing, and the connection devices form an intravenous (IV) set.

10. The cassette of claim 1, wherein the first inlet valve is in fluid communication with the first outlet valve only through the first pumping chamber.

11. An IV pump system, comprising:
a cassette, comprising:
an interface element having a first position and a second position and a slot that is oriented perpendicular to a direction of linear motion of the interface element between the first and second positions;
a first and a second pumping chamber each having a volume and each coupled to the interface element such that the volume of the first pumping chamber is increasing while the volume of the second pumping chamber is decreasing as the interface element moves from the first position to the second position and the volume of the first pumping chamber is decreasing while the volume of the second pumping chamber is increasing as the interface element moves from the second position to the first position;
an intake port and a delivery port;
a first and a second inlet valve coupled between the intake port and the respective pumping chambers;
a first and a second outlet valve coupled between the respective pumping chambers and the delivery port; and
an IV pump, comprising:
a housing comprising an attachment location configured to accept and retain the cassette; and
a driving element comprising an axis of rotation and a drive pin that is parallel to and offset from the axis of rotation, the drive pin configured to engage the slot of the interface element of the cassette when the cassette is retained in the attachment location such that the drive pin slides along a portion of the slot as the driving element rotates,
wherein the interface element is configured to be driven from the first position to the second position and back to the first position by unidirectional rotary motion of the driving element, and
wherein the inlet valves and the outlet valves are configured to be actuated via one or more elements disposed on a surface of the cassette facing the attachment location of the housing and to provide a continuous flow between the intake port and the delivery port.

12. The IV pump system of claim 11, wherein the drive pin follows a circular path about the axis of rotation as the driving element rotates.

13. The IV pump system of claim 11, wherein the cassette has a total internal volume between the intake port and the delivery port, and wherein the cassette is configured to create, when the driving element moves from either the first position to the second position or from the second position to the first position, a negative pressure at the intake port of at least 5 pounds per square inch below ambient pressure without a change in the total internal volume of the cassette.

14. The IV pump system of claim 11, wherein the IV pump further comprises:
a first and a second inlet valve actuator configured to actuate the first and second inlet valves, respectively, when the cassette is retained in the attachment location; and
a first and a second outlet valve actuator configured to actuate the first and second outlet valves, respectively, when the cassette is retained in the attachment location;
wherein the driving element, the inlet valve actuators, and the outlet valve actuators are configured to manipulate their respective elements of the cassette to cause fluid to move from the intake port to the delivery port.

15. The IV pump system of claim 14, wherein:
the inlet valves and the outlet valves are configured to stop flow when actuated by their respective valve actuators and allow flow when not actuated;
the second inlet valve actuator and the first outlet valve actuator actuate the second inlet and first outlet valves, respectively, while the interface element moves from the first position to the second position; and
the first inlet valve actuator and the second outlet valve actuator actuate the first inlet and second outlet valves, respectively, while the interface element moves from the second position to the first position.

16. The IV pump system of claim 15, wherein:
the driving element has an angular position; and
the valve actuators are coupled to the driving element such that the valve actuators actuate the valves of the cassette in a fixed relationship to the angular position of the driving element.

17. The IV pump system of claim 16, wherein driving element further comprises a cam that actuates at least one of the valve actuators.

18. The IV pump system of claim 11, wherein the driving element has a rotational speed that varies according to its angular position.

19. The IV pump system of claim 12, wherein:
the driving element further comprises a drive disk that rotates about the axis of rotation, wherein the drive pin is coupled to the drive disk;
the slot has a length; and
the drive pin slides along a portion of the length of the slot as the driving element rotates.

20. The IV pump system of claim 19, wherein:
the drive pin is movable relative to the drive disk between an extended position and a flush position;
the driving element further comprises a biasing element configured to urge the drive pin to move from the flush position to the extended position;
the drive pin will be forced to the flush position if the cassette is installed in the housing of the IV pump when the drive pin is not aligned with the slot; and
the drive pin will slide across the interface element as the drive disk rotates until the drive pin is aligned with the slot, whereupon the biasing element will cause the drive pin to move to the extended position and engage the slot.

21. The IV pump system of claim 19, wherein the interface element comprises a Scotch yoke.

22. The IV pump system of claim 11, wherein the first inlet valve is in fluid communication with the first outlet valve only through the first pumping chamber, and the second inlet valve is in fluid communication with the second outlet valve only through the second pumping chamber.

23. A cassette comprising:
an interface element having a first position and a second position, the interface element configured to be driven from the first position to the second position and back to the first position by unidirectional rotary motion of a driving element;

a first and a second pumping chamber each having a volume and each coupled to the interface element such that the volume of the first pumping chamber is increasing while the volume of the second pumping chamber is decreasing as the interface element moves from the first position to the second position and the volume of the first pumping chamber is decreasing while the volume of the second pumping chamber is increasing as the interface element moves from the second position to the first position;

an intake port and a delivery port;

a first and a second inlet valve coupled between the intake port and their respective pumping chambers; and a first and a second outlet valve coupled between their respective pumping chambers and the delivery port, wherein the inlet valves and the outlet valves are configured to be actuated via one or more elements disposed on an actuator-facing surface of the cassette, and to provide a continuous flow between the intake port and the delivery port.

24. The cassette of claim 23, wherein the one or more elements disposed on the actuator-facing surface of the cassette comprise one or more flexible elements.

* * * * *